United States Patent
Hu et al.

(10) Patent No.: US 10,796,237 B2
(45) Date of Patent: Oct. 6, 2020

(54) PATIENT-LEVEL ANALYTICS WITH SEQUENTIAL PATTERN MINING

(71) Applicant: INTERNATIONAL BUSINESS MACHINES CORPORATION, Armonk, NY (US)

(72) Inventors: Jianying Hu, Bronx, NY (US); Kun Lin, Bethesda, MD (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 848 days.

(21) Appl. No.: 15/195,465

(22) Filed: Jun. 28, 2016

(65) Prior Publication Data
US 2017/0372033 A1 Dec. 28, 2017

(51) Int. Cl.
| G06N 5/04 | (2006.01) |
| G16H 50/70 | (2018.01) |
| G06N 20/00 | (2019.01) |
| G06K 9/66 | (2006.01) |
| G06K 9/00 | (2006.01) |

(52) U.S. Cl.
CPC ............. *G06N 5/047* (2013.01); *G06N 20/00* (2019.01); *G16H 50/70* (2018.01); *G06K 9/00* (2013.01); *G06K 9/66* (2013.01); *G06N 5/04* (2013.01)

(58) Field of Classification Search
CPC .......... G06N 5/04; G06N 5/047; G06N 20/00; G06N 20/10; G06N 20/20; G16H 50/70; G06K 9/00; G06K 9/66
USPC ................................................ 706/11, 20, 48
See application file for complete search history.

(56) References Cited

U.S. PATENT DOCUMENTS

| 6,473,757 | B1 | 10/2002 | Garofalakis et al. | |
| 2005/0154710 | A1* | 7/2005 | Ruhlow | G06F 16/2454 |
| 2007/0050381 | A1* | 3/2007 | Hu | G06F 16/2237 |
| 2008/0275731 | A1 | 11/2008 | Rao et al. | |
| 2012/0117099 | A1 | 5/2012 | Gross | |
| 2013/0018672 | A1* | 1/2013 | Wong | G06F 19/328 |
| | | | | 705/3 |
| 2014/0257045 | A1 | 9/2014 | Hu et al. | |
| 2014/0297323 | A1 | 10/2014 | Hu et al. | |
| 2014/0297324 | A1 | 10/2014 | Duftler et al. | |
| 2015/0106022 | A1* | 4/2015 | Gotz | G16H 50/70 |
| | | | | 702/19 |

(Continued)

OTHER PUBLICATIONS

Gotz et al., A methodology for interactive mining and visual analysis of clinical event patterns using electronic health record data, Jan. 28, 2014, Journal of Biomedical Informatics, pp. 148-159. (Year: 2014).*

(Continued)

*Primary Examiner* — Shane D Woolwine
(74) *Attorney, Agent, or Firm* — Cantor Colburn LLP; Vazken Alexanian

(57) ABSTRACT

Examples of techniques for patient-level analytics with sequential pattern mining are provided. In one example implementation according to aspects of the present description, a computer-implemented method includes: constructing a patient record; transforming, by a processing system, the patient record into a bitmap representation; and analyzing, by the processing system, the bitmap to identify a sequential pattern within the patient record on a per patient basis.

25 Claims, 8 Drawing Sheets

(56) References Cited

U.S. PATENT DOCUMENTS

2017/0147664 A1\* 5/2017 Bussler .................. G06F 16/22

OTHER PUBLICATIONS

Ayres et al. "Sequential PAttern Mining using a Bitmap Representation," ACM SIGKDD International Conference, 2002, pp. 429-435.
Gotz et al., "A Methodology for Interactive Mining and Visual Analysis of Clinical Event Patterns Using Electronic Health Record Data," Journal of Biomedical Informatics 48, Apr. 2014, pp. 148-159.
Perer et al., "Mining and Exploring Care Pathways from Electronic Medical Records with Visual Analytics," Journal of Biomedical Informatics 56, 2015, pp. 369-378.
Adam Perer, et al., "Frequence: Interactive Mining and Visualization of Temporal Frequent Event Sequences", ACM 978-1-4503-2184-6/14/02; Feb. 24-27, 2014; 10 pages.
Ben Shneiderman; "The Eyes Have It a Task by Data Type Taxonomy for Information Visualizations"; Department of Computer Science, Human-Computer Interaction Laboratory, and Institute for Systems Research University of Maryland, College Park, Maryland, 1996 IEEE; pp. 336-334.

\* cited by examiner

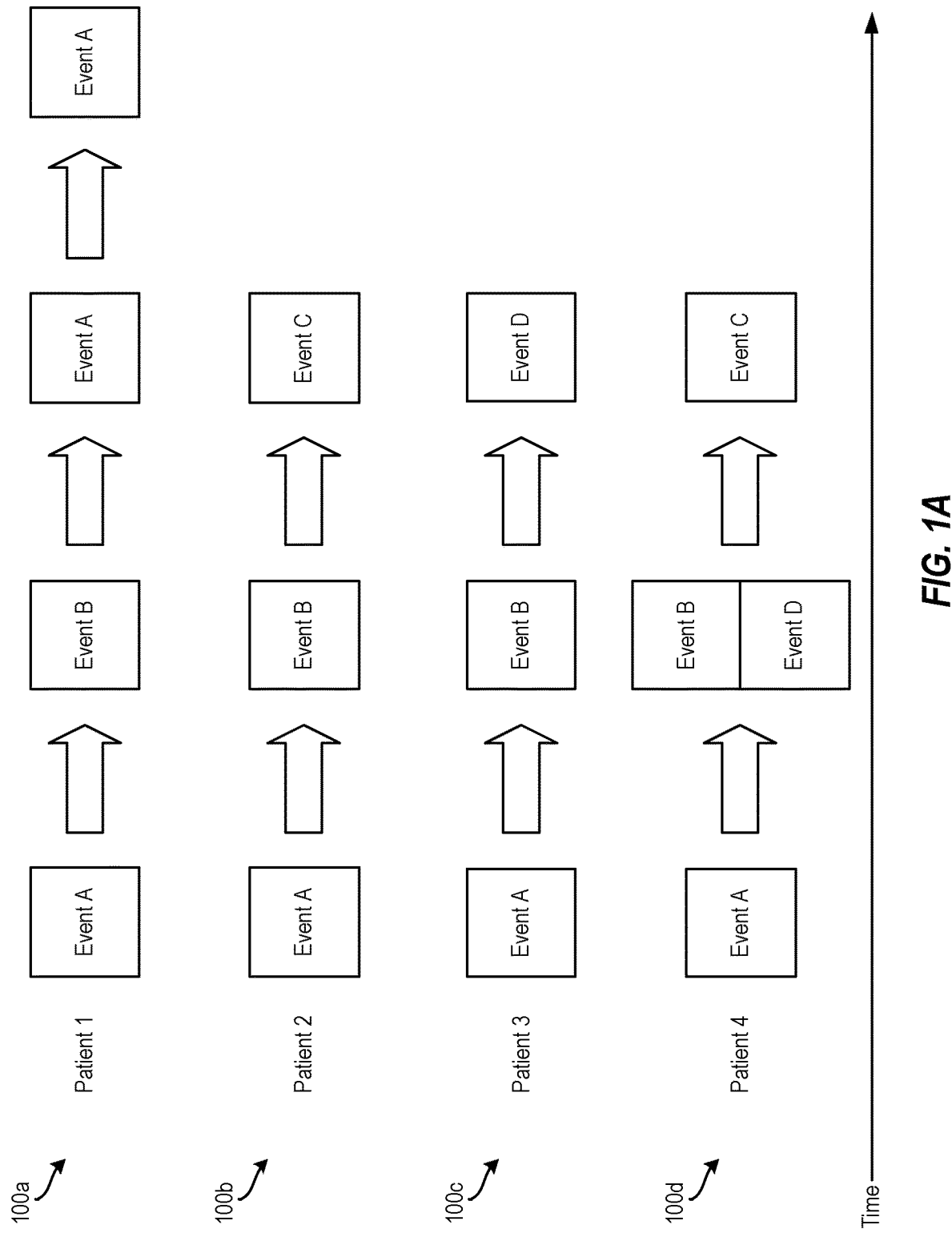

| PID | TS | {a} | {a}s | {b} | {a}, {b} |
|---|---|---|---|---|---|
| 1 | 1 | 1 | 0 | 1 | 0 |
| 1 | 2 | 0 | 1 | 1 | 1 |
| 1 | 3 | 0 | 1 | 1 | 1 |
| 1 | 4 | 0 | 1 | 0 | 0 |
| 2 | 1 | 0 | 0 | 1 | 0 |
| 2 | 2 | 1 | 0 | 1 | 0 |
| 2 | 3 | 0 | 1 | 0 | 0 |
| 2 | 4 | 0 | 1 | 0 | 0 |
| 3 | 1 | 1 | 0 | 1 | 0 |
| 3 | 2 | 0 | 1 | 1 | 1 |
| 3 | 3 | 0 | 1 | 0 | 0 |
| 3 | 4 | 0 | 1 | 0 | 0 |

Pattern: {a}, {b}
Count: 2 patients
Support: {PID1, PID3}

*FIG. 3*

PATIENT-LEVEL ANALYTICS WITH SEQUENTIAL PATTERN MINING

BACKGROUND

The present techniques relate to sequential pattern mining and, more particularly, to patient-level analytics with sequential pattern mining.

Sequential pattern mining identifies patterns within data where the values are delivered in a sequence. Sequential pattern mining is useful in the healthcare industry for example to identify patterns within patients' medical histories. Identifying patterns aids healthcare providers to diagnose and treat patients based on a patient's medical history and/or based on patterns identified in other patients.

SUMMARY

According to aspects of the present description, techniques including methods, systems, and/or computer program products for patient-level analytics with sequential pattern mining are provided.

In one embodiment of the present invention, a computer-implemented method includes: constructing a patient record; transforming, by a processing system, the patient record into a bitmap representation; and analyzing, by the processing system, the bitmap to identify a sequential pattern within the patient record on a per patient basis.

In another embodiment of the present invention, a computer-implemented method includes: constructing a plurality of patient records, wherein each patient record is associated with a patient ID; transforming, by a processing system, the plurality of patient records into a bitmap representation; analyzing, by the processing system, the bitmap to identify a sequential pattern within the patient record; and generating, by the processing system, a patient-based count of the identified sequential pattern.

The techniques for patient-level analytics with sequential pattern mining described herein provide the advantage of feature selection and construction for personalized, patient-level prediction. This enables mapping each pattern-level cohort into its corresponding patient-level cohort. This also enables performing feature construction and selection on each patient-level cohort, using machine learning techniques, for example. This provides the additional advantage of enabling a healthcare provider to determine who (i.e., which patient) experienced a certain pattern.

In additional aspects of the present techniques, analyzing the bitmap further comprises identifying an occurrence of a first event within the bitmap, identifying an occurrence of a second event within the bitmap, and comparing the occurrence of the first event to the occurrence of the second event. The sequential pattern is identified when the second event occurs at a time after the first event. This provides the advantage of enabling a healthcare provider to determine who (i.e., which patient) experienced a certain pattern.

In yet additional aspects of the present techniques, the patient-based count comprises a number of patients for which the sequential pattern occurred and the patient ID for each of the corresponding patients. This provides the advantage of enabling a healthcare provider to determine who (i.e., which patient) experienced a certain pattern.

It should also be appreciated that the present techniques provide for faster sequential pattern mining than previous approaches. This reduces the amount of computational time and system resources (e.g., memory, processor, etc.) needed by a processing system.

Additional features and advantages are realized through the techniques of the present description. Other aspects are described in detail herein and are considered a part of the description. For a better understanding of the present description with the advantages and the features, refer to the following description and to the drawings.

BRIEF DESCRIPTION OF THE DRAWINGS

The subject matter which is regarded as the invention is particularly pointed out and distinctly claimed in the claims at the conclusion of the specification. The foregoing and other features, and advantages thereof, are apparent from the following detailed description taken in conjunction with the accompanying drawings in which:

FIG. 1A illustrates a block diagram of event sequences for patients according to aspects of the present description;

FIG. 3 illustrates an analysis of a bitmap according to aspects of the present description;

DETAILED DESCRIPTION

Figure 1B:
FIG. 1B illustrates the sequential patterns determined based on the event sequences of FIG. 1A according to aspects of the present description.
Figure 1B:
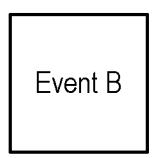
Figure 1B:
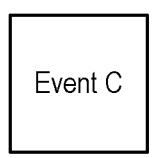
Figure 1B:
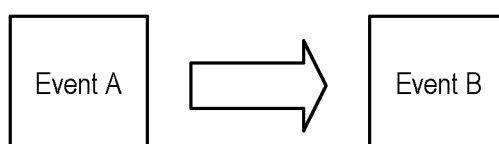
Figure 1B:
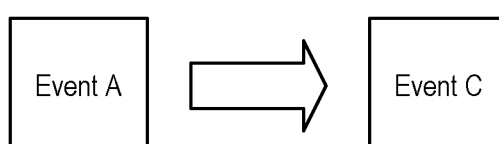
Figure 1B:
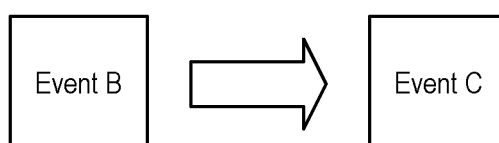
Figure 1B:
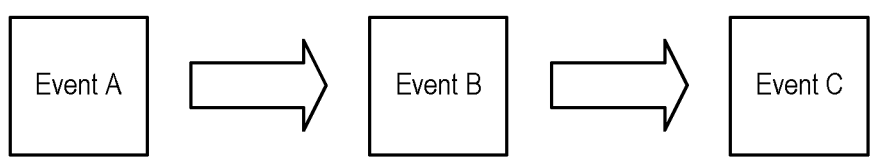

The present description relates to using sequential pattern mining for patient analytics. Sequential pattern mining provides understanding of the temporal aspects of a patient. For example, it can be desirable to understand the relationship between a patient's medical history and an outcome (e.g., a diagnosed condition).

Existing sequential pattern mining techniques fail to provide understanding of the relationship between a patient's medical history and an outcome. Instead, existing techniques mostly concentrate on counting occurrences of a particular pattern. The present description provides for a better understanding of such a relationship by detecting pattern frequencies within a patient's medical history and within multiple patients' medical histories. The present techniques provide the ability to determine which patient experienced a multiple pattern and how often a potential pattern occurred (within a patient and within a set of patients).

The present techniques provide for faster sequential pattern mining than previous approaches. This reduces the amount of computational time and system resources (e.g., memory, processor, etc.) needed by a processing system. In fact, the present techniques provide the additional benefit of providing pattern frequency without using any additional system resources (e.g., memory, processor, etc.) than existing approaches that only provide pattern counts. These and other advantages will be apparent from the description that follows.

Turning now to an overview of the present description, one or more embodiments provide a methodology for constructing a patient record that is transformed into a bitmap representation. The bitmap representation is then analyzed to identify sequential patterns on a per patient basis. During the analysis, events are identified and compared, for example, using an AND operation. A patient-based count can be generated to indicate how many patients experienced the sequential pattern. By identifying sequential patterns on a per patient basis, more accurate pattern counting is possible. For example, the identified sequential patterns are useful for feature selection and construction for personalized, patient-level prediction.

FIG. 1A illustrates a block diagram of event sequences 100a, 100b, 100c, and 100d for patients according to aspects of the present description. In particular, event sequences 100a, 100b, 100c, 100d (collectively "event sequences 100") are illustrated for four patients: Patient 1, Patient 2, Patient 3, and Patient 4. It should be appreciated that, in the example illustrated in FIG. 1, the event sequences 100 are illustrated as occurring with respect to a time line, with the events on the left of the figure occurring earlier in time than events on the right of the figure. It should also be appreciated that the events can occur at different times for each patient and that the events may not align as illustrated in FIG. 1A.

The events represent events that occur in a patient's medical history. For example, Event A represents an elevated temperature, Event B represents a headache, Event C represents an increased white blood cell count, and Event D represents vomiting. These can be symptoms of an illness. In other examples, other events are possible. The present techniques provide for sequential pattern mining to detect the occurrence and frequency of patterns based on patients' medical history.

For example, FIG. 1B illustrates the sequential patterns 101 determined based on the event sequences 100 of FIG. 1A according to aspects of the present description. In the example of FIG. 1B, each of the event sequences 100 with a frequency threshold of at least 60% occurrence are illustrated. It should be appreciated that the frequency threshold is adjustable and can be lower or higher than the 60% threshold illustrated in FIG. 1B.

The following sequential patterns are illustrated in FIG. 1B: Event A; Event B; Event C; Event A→Event B; Event A→Event C; Event B→Event C; Event A→Event B→Event C.

Events A and B both occur at least once in each of the patients, and thus has a frequency of 100%. Event C occurs in 3 of the 4 patients (not Patient 3), and thus has a frequency of 75%. Event D, however, occurs only in two patients (Patient 3 and Patient 4) and thus has a frequency of 50%, less than the 60% threshold used in FIG. 1B. Therefore, Events A, B, and C are illustrated as sequential patterns in FIG. 1B, and Event D is not. Similarly, the sequential pattern of Events A followed by (→) Event B occurs in each of the four patients and therefore is illustrated in FIG. 1B. It should be appreciated that the other sequential patterns illustrated in FIG. 1B occur in at least 60% of the patients based on the frequency threshold of 60% used in FIG. 1B.

Turning to FIG. 3, a bitmap 300 of patient records 301, 302, 303 according to aspects of the present description is shown. It should be appreciated that patient record 301 corresponds to patient ID (PID) 1, patient record 302 corresponds to PID 2, and patient record 303 corresponds to PID 3.

Figure 2:
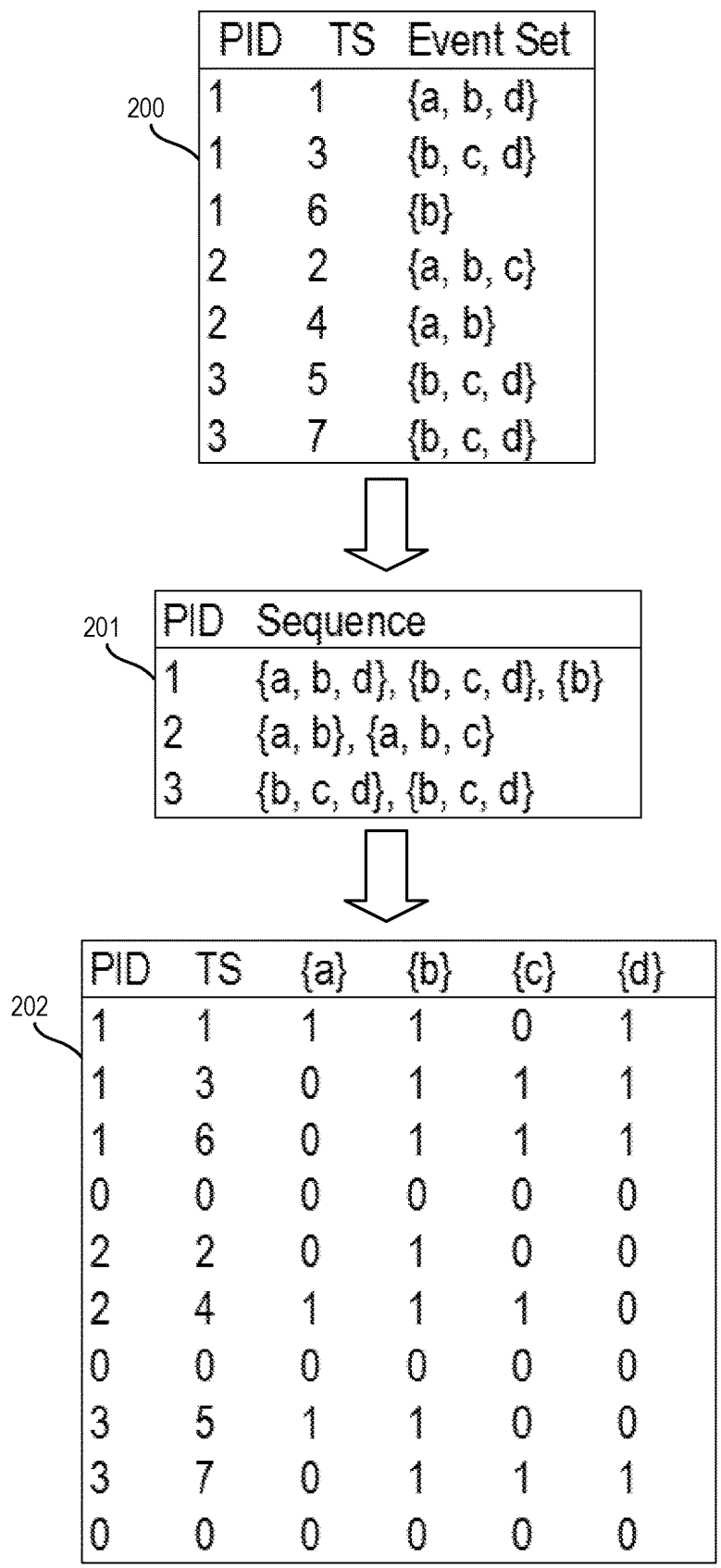
FIG. 2 illustrates a patient record being transformed into a bitmap 202 according to aspects of the present description.

FIG. 2 illustrates a patient record 200 being transformed into a bitmap 202 according to aspects of the present description. The patient record 200 corresponds to three patients denoted by patient IDs (PID): PID1, PID2, and PID3. The patient record 200 contains individual event set records for each PID at corresponding time stamps (TS). For example, the patient record 200 contains an event set record for event set {a, b, d} for PID1 at TS1. Similarly, the patient record 200 contains an event set record for event set {b, c, d} for PID3 at TS5. The patient record 200 also contains an event set record for event set {b, c, d} for PID3 at TS7, indicating that the patient associated with PID3 experienced event set {b, c, d} at two different times (i.e., TS5 and TS7). It should be appreciated that the patient record 200 contains additional event set records as illustrated in FIG. 2.

The patient record 200 is transformed into a sequence table 201 using the present techniques to identify each of the event sets for each of the patients. For example, as shown in the sequence table 201, patient 1 (i.e., PID1) experienced event sets {a, b, d}, {b, c, d}, and Patient 2 (i.e., PID2) experienced event sets {a, b} and {a, b, c}. Patient 3 (i.e., PID3) experienced event set {b, c, d} two times.

The sequence table 201 is then transformed into a bitmap 202. The bitmap 202 displays each PID and TS with the corresponding events of the event set for the respective PID and TS. For example, PID1 at TS1 shows events {a}, {b}, and {d} occurring (i.e., event set {a, b, D}). In another example, PID2 at TS4 shows events {a}, {b}, and {c} occurring (i.e., event set {a, b, c}).

In the example of FIG. 2, the rows of zeros between PID1 and PID2 and between PID2 and PID3 act as indicators between the PIDs. In other examples, other indicators can be used, or the indicators can be omitted.

It should be appreciated that the bitmap 202 can contain details for additional patients (additional PIDs) and additional events.

FIG. 3 illustrates an analysis of a bitmap 300 according to aspects of the present description. The bitmap 300 includes patient records for patient 301 (i.e., PID1), patient 302 (i.e., PID2), and patient 303 (i.e., PID3).

In this example, the analysis is attempting to identify a sequential pattern of event {a} occurring prior to event {b} occurring (denoted {a}, {b}). For the first time stamp when event {a} occurs for a patient, the value of column {a}s is set to 0. However, for each subsequent time stamp, {a}s is set to 1 to indicate that event {a} already occurred. Then, by comparing column {a}s to column {b} using an AND operation, it can be determined whether the event sequence pattern {a}, {b} occurred.

In the case of patient 301 as an example, four TS entries for PID1 exist: TS1, TS2, TS3, and TS4. It can be seen then, at TS1 for PID1, event {a} occurs (shown as column {a}) and event {b} occurs. Because event {a} occurs, {a}s is set to 0. Therefore, when column {a}s is compared to column {b} using the AND operation, the result is 0.

Continuing with patient 301, at TS2, {a}s is set to 1 because event {a} occurred at TS1. At TS2, event {b} occurred. Therefore, when column {a}s is compared to column {b} using the AND operation, the result is 1. This indicates an occurrence of the pattern {a}, {b}.

At TS3 of patient 301, {a}s remains 1 because event {a} occurred at TS1. At TS3, event {b} occurred. Therefore, when column {a}s is compared to column {b} using the AND operation, the result is 1. This indicates an occurrence of the pattern {a}, {b}.

Finally, at TS4 of patient 301, {a}s remains 1 because event {a} occurred at TS1. At TS3, event {b} does not occur. Therefore, when column {a}s is compared to column {b} using the AND operation, the result is 0, which does not indicate an occurrence of the pattern {a}, {b}.

Therefore, for patient 301 (PID1), the total count for the pattern {a}, {b} is 2. Using the same techniques, the total count for the pattern {a}, {b} for patient 302 (PID2) is 0 and the total count for the pattern {b} for patient 303 (PID3) is 1.

Using traditional sequential pattern counting techniques, the result is 3 occurrences of the pattern {a}, {b}. However, by applying the present techniques on a patient ID basis, it can be appreciated that the patent count for the number of occurrences of the pattern {a}, {b} is 2. So although the pattern {a}, {b} occurred three times, it only occurred in two different patients (PID 1 and PID3).

By analyzing patent records on a per patient basis, patterns can be detected per patient. By detecting patterns per patient, healthcare providers are able to more accurately recognize patterns and treat patients. For example, if a pattern count is high, it can indicate that one patient experienced the pattern multiple times but that the pattern may not be true for a population.

Figure 4:
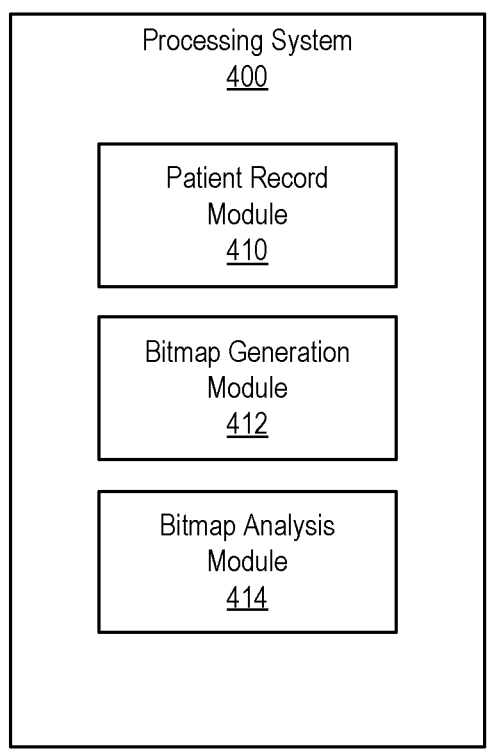
FIG. 4 illustrates a block diagram of a processing system for patient-level analytics with sequential pattern mining according to aspects of the present description.

FIG. 4 illustrates a block diagram of a processing system 400 for patient-level analytics with sequential pattern mining according to aspects of the present description. The various components, modules, engines, etc. described regarding FIG. 4 can be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these. In examples, the engine(s) described herein can be a combination of hardware and programming. The programming can be processor executable instructions stored on a tangible memory, and the hardware can include a processing device for executing those instructions. Thus a system memory can store program instructions that when executed by a processing device implement the engines described herein. Other engines can also be utilized to include other features and functionality described in other examples herein.

Processing system 100 can include a patient record module 410, a bitmap generation module 412, and a bitmap analysis module 414. Generally, the patent record module 410 constructs a patient record. The bitmap generation module 412 transforms the patient record into a bitmap representation. The bitmap analysis module 414 analyzes the bitmap to identify a sequential pattern within the patient record. Additional functional details of the processing system 400 are discussed below regarding FIG. 5 and FIG. 6.

Alternatively or additionally, the processing system 100 can include dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein.

Figure 5:
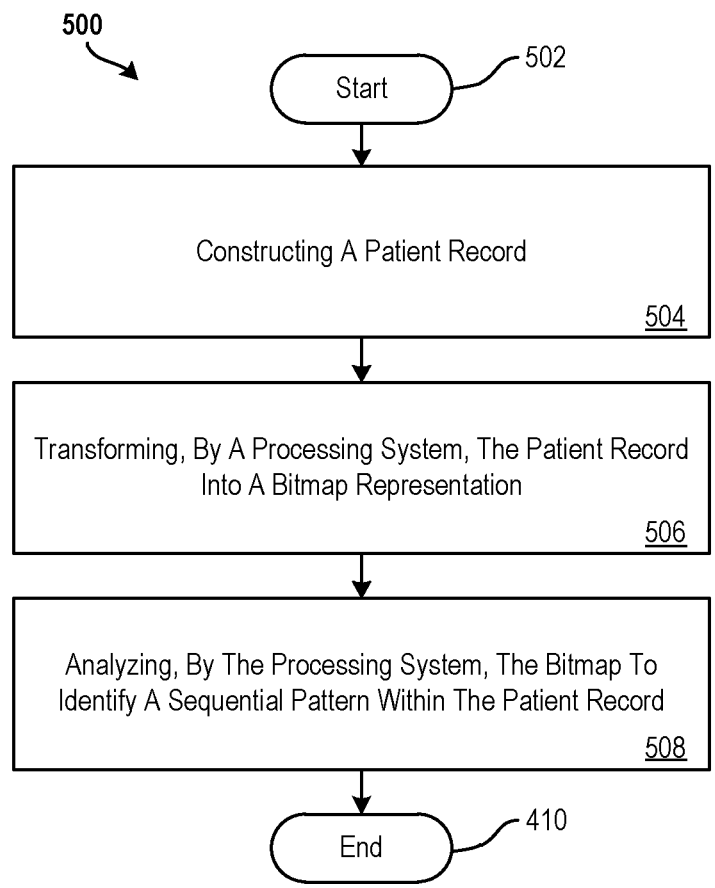
FIG. 5 illustrates a flow diagram of a method for patient-level analytics with sequential pattern mining according to aspects of the present description.

FIG. 5 illustrates a flow diagram of a method 500 for patient-level analytics with sequential pattern mining according to aspects of the present description. The method 500 can be performed, for example, by the processing system 400 of FIG. 4, by the processing system 20 of FIG. 7, and/or by another suitable processing system. The method 500 starts at block 502 and continues to block 504.

At block 504, the method 500 includes constructing a patient record. In some examples, the patient record includes a patient ID, a timestamp, and an event, although the patient record can include other information in other examples.

At block 506, the method 500 includes transforming, by the processing system, the patient record into a bitmap representation, such at the bitmap 202 of FIG. 2.

At block 508, the method 500 includes analyzing, by the processing system, the bitmap to identify a sequential pattern within the patient record on a per patient basis. In examples, analyzing the bitmap further includes identifying an occurrence of a first event and a second event within the bitmap. Additionally, analyzing the bitmap further includes comparing the occurrence of the first event to the occurrence of the second event, wherein the sequential pattern is identified when the second event occurs at a time after the first event. In other examples, analyzing the bitmap further comprises determining a frequency of the sequential pattern within the patient record.

The method 500 proceeds to block 510 and ends. However, additional processes also can be included. For example, the pattern can be displayed on a display of the processing system. In some examples, in addition to the pattern, the patient IDs for the patient records having the pattern are also displayed. It should be understood that the processes depicted in FIG. 5 represent illustrations, and that other processes can be added or existing processes can be removed, modified, or rearranged without departing from the scope and spirit of the present description.

Figure 6:
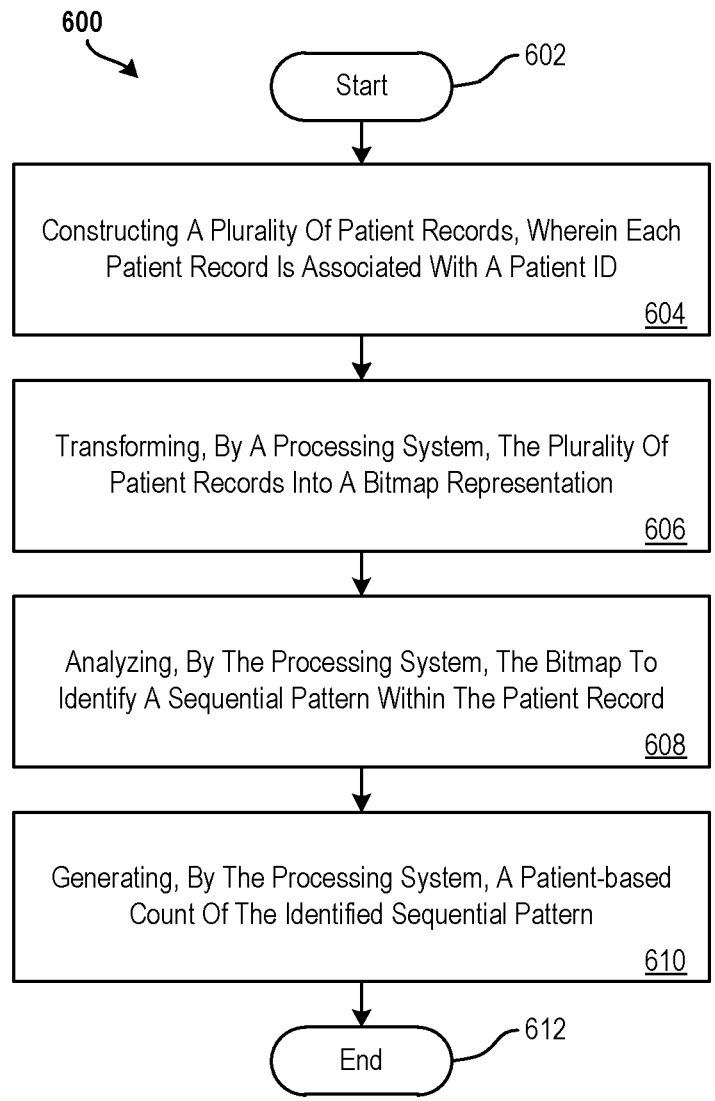
FIG. 6 illustrates a flow diagram of a method for patient-level analytics with sequential pattern mining according to aspects of the present description.

FIG. 6 illustrates a flow diagram of a method 600 for patient-level analytics with sequential pattern mining according to aspects of the present description. The method 600 can be performed, for example, by the processing system 400 of FIG. 4, by the processing system 20 of FIG. 7, and/or by another suitable processing system. The method 600 starts at block 602 and continues to block 604.

At block 604, the method 600 includes constructing a plurality of patient records, wherein each patient record is associated with a patient ID.

At block 606, the method 600 includes transforming, by a processing system, the plurality of patient records into a bitmap representation.

At block 608, the method 600 includes analyzing, by the processing system, the bitmap to identify a sequential pattern within the patient record.

At block 610, the method 600 includes generating, by the processing system, a patient-based count of the identified sequential pattern. In examples, the patient-based count includes a number of patients for which the sequential pattern occurred and the patient ID for each of the corresponding patients.

The method 600 proceeds to block 612 and ends. However, additional processes also can be included, and it should be understood that the processes depicted in FIG. 6 represent illustrations, and that other processes can be added or existing processes can be removed, modified, or rearranged without departing from the scope and spirit of the present description.

The present techniques provide numerous advantages over existing approaches. For example, the identified sequential patterns are useful for feature selection and construction for personalized, patient-level prediction. This enables mapping each pattern-level cohort into its corresponding patient-level cohort. This also enables performing feature construction and selection on each patient-level cohort, using machine learning techniques, for example. The present techniques enable a healthcare provider to determine who (i.e., which patient) experienced a certain pattern.

It should be understood that the present techniques enable significantly reducing the overall execution time of the machine learning pipeline by performing patient-level analysis and pattern mining in parallel.

Figure 7:
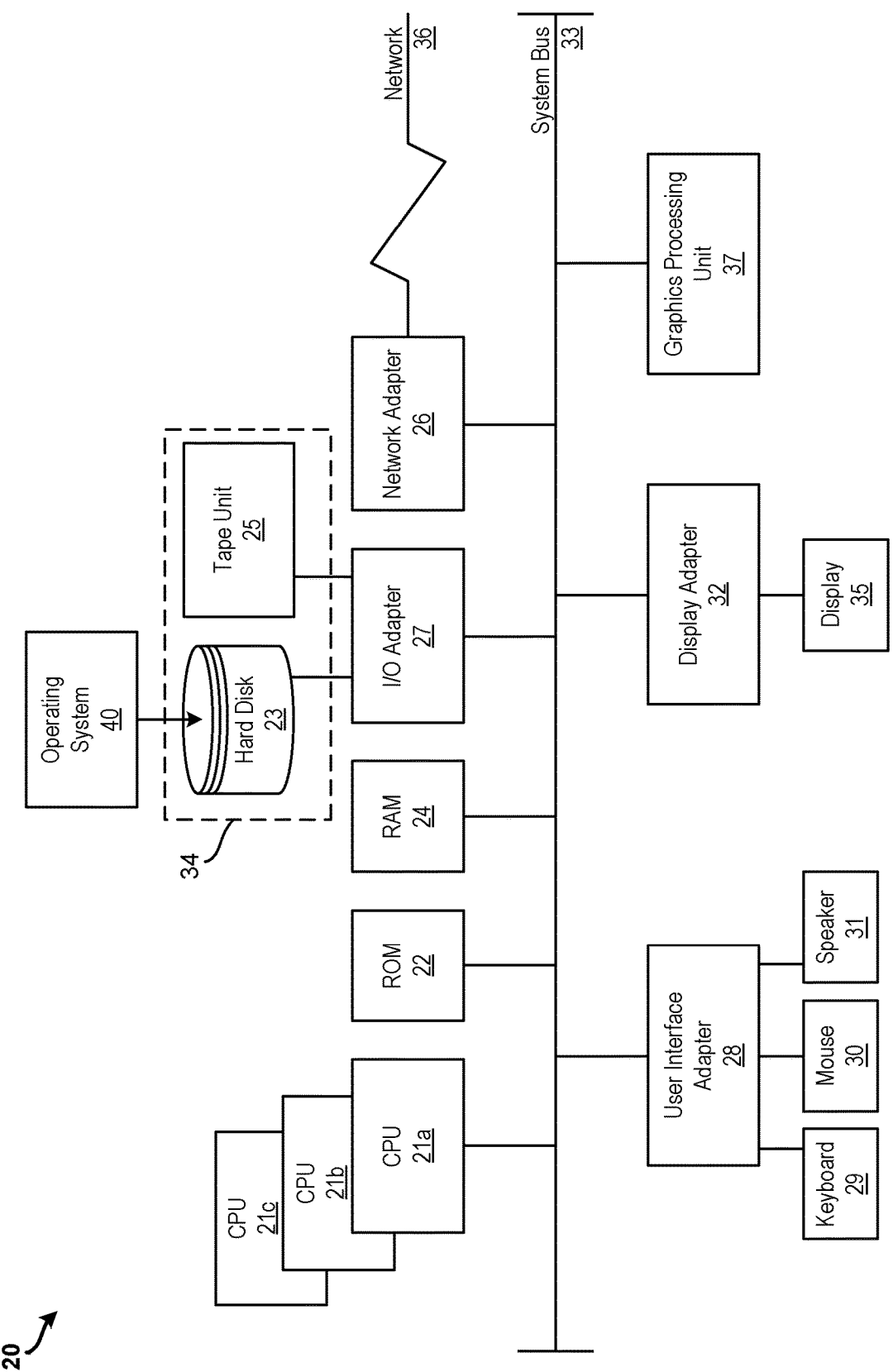
FIG. 7 illustrates a block diagram of a processing system for implementing the techniques described herein according to aspects of the present description.

It is understood in advance that the present description is capable of being implemented in conjunction with any other type of computing environment now known or later developed. For example, FIG. 7 illustrates a block diagram of a processing system 20 for implementing the techniques described herein. In examples, processing system 20 has one or more central processing units (processors) 21a, 21b, 21c, etc. (collectively or generically referred to as processor(s) 21 and/or as processing device(s)). In aspects of the present description, each processor 21 can include a reduced instruction set computer (RISC) microprocessor. Processors 21 are coupled to system memory (e.g., random access memory (RAM) 24) and various other components via a system bus 33. Read only memory (ROM) 22 is coupled to system bus 33 and can include a basic input/output system (BIOS), which controls certain basic functions of processing system 20.

Further illustrated are an input/output (I/O) adapter 27 and a communications adapter 26 coupled to system bus 33. I/O adapter 27 can be a small computer system interface (SCSI) adapter that communicates with a hard disk 23 and/or a tape storage drive 25 or any other similar component. I/O adapter 27, hard disk 23, and tape storage device 25 are collectively referred to herein as mass storage 34. Operating system 40 for execution on processing system 20 can be stored in mass storage 34. A network adapter 26 interconnects system bus 33 with an outside network 36 enabling processing system 20 to communicate with other such systems.

A display (e.g., a display monitor) 35 is connected to system bus 33 by display adaptor 32, which can include a graphics adapter to improve the performance of graphics intensive applications and a video controller. In one aspect of the present description, adapters 26, 27, and/or 32 can be connected to one or more I/O busses that are connected to system bus 33 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 33 via user interface adapter 28 and display adapter 32. A keyboard 29, mouse 30, and speaker 31 can be interconnected to system bus 33 via user interface adapter 28, which can include, for example, a Super I/O chip integrating multiple device adapters into a single integrated circuit.

In some aspects of the present description, processing system 20 includes a graphics processing unit 37. Graphics processing unit 37 is a specialized electronic circuit designed to manipulate and alter memory to accelerate the creation of images in a frame buffer intended for output to a display. In general, graphics processing unit 37 is very efficient at manipulating computer graphics and image processing, and has a highly parallel structure that makes it more effective than general-purpose CPUs for algorithms where processing of large blocks of data is done in parallel.

Thus, as configured herein, processing system 20 includes processing capability in the form of processors 21, storage capability including system memory (e.g., RAM 24), and mass storage 34, input means such as keyboard 29 and mouse 30, and output capability including speaker 31 and display 35. In some aspects of the present description, a portion of system memory (e.g., RAM 24) and mass storage 34 collectively store an operating system such as the AIX® operating system from IBM Corporation to coordinate the functions of the various components shown in processing system 20.

The present techniques ma can y be implemented as a system, a method, and/or a computer program product. The computer program product can include a computer readable storage medium (or media) having computer readable program instructions thereon for causing a processor to carry out aspects of the present description.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present description can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some examples, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present description.

Aspects of the present description are described herein with reference to flowchart illustrations and/or block diagrams of methods, apparatus (systems), and computer program products according to aspects of the present description. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the present description. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present description have been presented for purposes of illustration, but are not intended to be exhaustive or limited to the embodiments described. Many modifications and variations will be apparent to those of ordinary skill in the art without departing from the scope and spirit of the described techniques. The terminology used herein was chosen to best explain the principles of the present techniques, the practical application or technical improvement over technologies found in the marketplace, or to enable others of ordinary skill in the art to understand the techniques described herein.

What is claimed is:

1. A computer-implemented method for patient-level analytics with sequential pattern mining, the method comprising:
   transforming, by a processing system, a patient record into a sequence table that identifies the event sets for a plurality of patients, the patient record comprising event sets for the plurality of patients;
   transforming, by the processing system, the sequence table into a bitmap representation, wherein the bitmap representation displays each of the event sets, each of the event sets being displayed as one or more events, and wherein the bitmap representation further displays, for each of the event sets, a corresponding patientID and a corresponding timestamp, the corresponding timestamp being associated with a time at which a corresponding event set for the corresponding patient ID occurred; and
   analyzing, by the processing system, the bitmap to identify a sequential pattern within the patient record on a per patient basis.

2. The computer-implemented method of claim 1, wherein analyzing the bitmap further comprises identifying an occurrence of a first event within the bitmap.

3. The computer-implemented method of claim 2, wherein analyzing the bitmap further comprises identifying an occurrence of a second event within the bitmap.

4. The computer-implemented method of claim 3, wherein analyzing the bitmap further comprises comparing the occurrence of the first event to the occurrence of the second event, wherein the sequential pattern is identified when the second event occurs at a time after the first event.

5. The computer-implemented method of claim 4, wherein analyzing the bitmap further comprises applying an AND operation to compare the occurrence of the first event and the occurrence of the second event.

6. The computer-implemented method of claim 1, further comprising:
   displaying, on a display, the identified pattern.

7. The computer-implemented method of claim 1, wherein analyzing the bitmap further comprises determining a frequency of the sequential pattern within the patient record.

8. The computer-implemented method of claim 1, further comprising constructing the patient record.

9. The computer-implemented method of claim 1, wherein the bitmap representation displays a patient ID column storing the patient IDs, a timestamp column storing the timestamps, and columns for each event of the event sets.

10. A system for patient-level analytics with sequential pattern mining, the system comprising:
   a memory having computer readable instructions; and
   a processing device for executing the computer readable instructions, the computer readable instructions comprising:
      transforming a patient record into a sequence table that identifies the event sets for a plurality of patients, the patient record comprising event sets for the plurality of patients;

transforming the sequence table into a bitmap representation, wherein the bitmap representation displays each of the event sets, each of the event sets being displayed as one or more events, and wherein the bitmap representation further displays, for each of the event sets, a corresponding patientID and a corresponding timestamp, the corresponding timestamp being associated with a time at which a corresponding event set for the corresponding patient ID occurred; and analyzing the bitmap to identify a sequential pattern within the patient record on a per patient basis.

11. The system of claim 10, wherein analyzing the bitmap further comprises identifying an occurrence of a first event within the bitmap.

12. The system of claim 11, wherein analyzing the bitmap further comprises identifying an occurrence of a second event within the bitmap.

13. The system of claim 12, wherein analyzing the bitmap further comprises comparing the occurrence of the first event to the occurrence of the second event, wherein the sequential pattern is identified when the second event occurs at a time after the first event.

14. The system of claim 13, wherein analyzing the bitmap further comprises applying an AND operation to compare the occurrence of the first event and the occurrence of the second event.

15. The system of claim 10, further comprising:
displaying, on a display, the identified pattern.

16. The system of claim 10, wherein analyzing the bitmap further comprises determining a frequency of the sequential pattern within the patient record.

17. A computer program product for patient-level analytics with sequential pattern mining, the computer program product comprising:
a computer readable storage medium having program instructions embodied therewith, the program instructions executable by a processing device to cause the processing device to:
transform a patient record into a sequence table that identifies the event sets for a plurality of patients of the patient record, the patient record comprising event sets for the plurality of patients;
transforming the sequence table into a bitmap representation, wherein the bitmap representation displays each of the event sets, each of the event sets being displayed as one or more events, and wherein the bitmap representation further displays, for each of the event sets, a corresponding patientID and a corresponding timestamp, the corresponding timestamp being associated with a time at which a corresponding event set for the corresponding patient ID occurred; and
analyze the bitmap to identify a sequential pattern within the patient record on a per patient basis.

18. The computer program product of claim 17, wherein analyzing the bitmap further comprises identifying an occurrence of a first event within the bitmap.

19. The computer program product of claim 18, wherein analyzing the bitmap further comprises identifying an occurrence of a second event within the bitmap.

20. The computer program product of claim 19, wherein analyzing the bitmap further comprises comparing the occurrence of the first event to the occurrence of the second event, wherein the sequential pattern is identified when the second event occurs at a time after the first event.

21. The computer program product of claim 20, wherein analyzing the bitmap further comprises applying an AND operation to compare the occurrence of the first event and the occurrence of the second event.

22. A computer-implemented method for patient-level analytics with sequential pattern mining, the method comprising:
transforming, by a processing system, a plurality of patient records into a sequence table that identifies event sets for a plurality of patients, the plurality of patient records comprising event sets for the plurality of patients;
transforming, by the processing system, the sequence table into a bitmap representation, wherein the bitmap representation displays each of the event sets, each of the event sets being displayed as one or more events, and wherein the bitmap representation further displays, for each of the event sets, a corresponding patientID and a corresponding timestamp, the corresponding timestamp being associated with a time at which a corresponding event set for the corresponding patient ID occurred;
analyzing, by the processing system, the bitmap to identify a sequential pattern within the plurality of patient records; and
generating, by the processing system, a patient-based count of the identified sequential pattern.

23. The computer-implemented method of claim 22, wherein the patient-based count comprises a number of patients for which the sequential pattern occurred and the patient ID for each of the corresponding patients.

24. The computer-implemented method of claim 22, wherein analyzing the bitmap further comprises comparing an occurrence of a first event to the occurrence of a second event to identify the sequential pattern.

25. A system for patient-level analytics with sequential pattern mining, the system comprising:
a memory having computer readable instructions; and
a processing device for executing the computer readable instructions, the computer readable instructions comprising:
transforming a plurality of patient records into a sequence table that identifies event sets for a plurality of patients, the plurality of patient records comprising event sets for the plurality of patients;
transforming the sequence table into a bitmap representation, wherein the bitmap representation displays each of the event sets, each of the event sets being displayed as one or more events, and wherein the bitmap representation further displays, for each of the event sets, a corresponding patientID and a corresponding timestamp, the corresponding timestamp being associated with a time at which a corresponding event set for the corresponding patient ID occurred;
analyzing the bitmap to identify a sequential pattern within the plurality of patient records; and
generating a patient-based count of the identified sequential pattern.

* * * * *